United States Patent [19]

Bartlett et al.

[11] Patent Number: 5,504,084
[45] Date of Patent: Apr. 2, 1996

[54] PHARMACEUTICAL FOR THE TREATMENT OF SKIN DISORDERS

[75] Inventors: Robert R. Bartlett, Darmstadt; Klaus U. Weithmann, Hofheim, both of Germany; Ellen S. Kurtz, Flemington, N.J.

[73] Assignees: Hoechst Aktiengesellschaft, Frankfurt am Main, Germany; Hoechst-Roussel Pharmaceuticals, Inc., North Somerville, N.J.

[21] Appl. No.: 216,332

[22] Filed: Mar. 23, 1994

Related U.S. Application Data

[63] Continuation-in-part of Ser. No. 41,223, Mar. 31, 1993, abandoned.

[51] Int. Cl.$^6$ .................. A61K 31/535; A61K 31/42; A61K 31; A61K 275
[52] U.S. Cl. .................. 514/236.8; 514/378; 514/521; 514/861; 514/863
[58] Field of Search .................. 514/236.8, 378, 514/521, 861, 863

[56] References Cited

U.S. PATENT DOCUMENTS

| | | | |
|---|---|---|---|
| 4,061,767 | 12/1977 | Ertel et al. | 424/282 |
| 4,351,841 | 9/1972 | Kammerer et al. | 424/272 |
| 5,001,124 | 3/1991 | Patterson et al. | 514/236.8 |
| 5,240,960 | 8/1993 | Hambleton et al. | 514/521 |
| 5,268,382 | 12/1993 | Bartlett et al. | 514/378 |

FOREIGN PATENT DOCUMENTS

| | | |
|---|---|---|
| 0013376A2 | 7/1980 | European Pat. Off. . |
| 0217206A2 | 4/1987 | European Pat. Off. . |
| 0257882A1 | 3/1988 | European Pat. Off. . |
| 0413329A2 | 2/1991 | European Pat. Off. . |
| 048423A2 | 5/1992 | European Pat. Off. . |
| 0583783A1 | 4/1993 | European Pat. Off. . |
| WO91/17748 | 11/1991 | WIPO . |

OTHER PUBLICATIONS

Chemical Abstracts (93:239393n) 1980.
Chemical Abstracts, vol. 115, 1991, p. 452, No. 115:1563ly.
Borel et al., Transplantation Proceedings, vol. 23, No. 2 (April), 1991:pp. 1867–1874.
Mason, Pharmacological Reviews, vol. 42, No. 3, 1989, pp. 423–434.
Hambleton and McMahon, "Drug Actions on Delayed–Type Hypersensitivity in Rats with Developing and Established Adjuvant Arthritis," Agents and Actions, vol. 29, 3/4 (1990), pp. 328–332.
Bartlett et al., "Effects of Lefluonomide on Immune Responses and Models of Inflammation," Springer Semin Immunopathol, (1993) 14:381–394.
Bartlett et al., "Lefluonomide (HWA 486), a Novel Immunomodulating Compound for the Treatment of Autoimmune Disorders and Reactions Leading to Transplantation Rejection," Agents and Actions, vol. 32, 1/2 (1991) pp. 10–21.
FASEB, vol. 4, No. 7, 1990, No. 2966.
Levitzki and Gilon, "Tryphostins as Molecular Tools and Potential Anti–proliferative drugs," Trends in Pharmaceutical Sciences, vol. 12, No. 5, 1991, pp. 171–174.
King and Stoscheck, "Epidermal Growth Factor: Its Relevance to Dermatology," J. Toxicol.–Cut. & Ocular Toxicol. 8(4), 411–416 (1989–1990).
Scholemmer et al., "Prolongation of Allogeneic Transplanted Skin Grafts and Induction of Tolerance by Lefluonomide, a New Immunosuppresive Isoxazol Derivative," Transplantation Proceedings, vol. 25, No. 1, Feb. 1993, pp. 763–767.
Enqst et al., "Stellenwert Immunsuppressiv Wirkender Pharmaka In Der Antipsoriatischen Therapie," Zeitschrift Fur Hautkrankheiten, vol. 66, No. 2, 1991, pp. 55–60.

Primary Examiner—Marianne M. Cintins
Assistant Examiner—K. Weddington
Attorney, Agent, or Firm—Finnegan, Henderson, Farabow, Garrett & Dunner

[57] ABSTRACT

Pharmaceutical for the treatment of skin disorders

A compound of the formula I or II

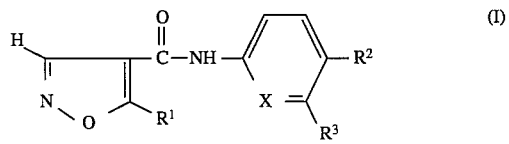

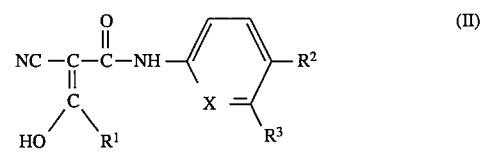

and physiologically tolerable salts of compound of the formula II are suitable for treatment of psoriasis.

16 Claims, No Drawings

PHARMACEUTICAL FOR THE TREATMENT OF SKIN DISORDERS

This application is a continuation-in-part of U.S. patent application Ser. No. 08/041,223 filed Mar. 31, 1993, now abandoned.

European Patent 13,376 discloses N-(4-trifluoromethylphenyl)-5-methylisoxazole-4-carboxamide (compound 1) as being anti-inflammatory. Processes for the preparation of this compound are also described therein.

It is additionally known that the compound 1 and N-(4-trifluoromethylphenyl)-2-cyano-3ohydroxycrotonamide (compound 2) have immunomodulation properties, so that they are suitable as pharmaceutical against chronic graft versus host diseases and against autoimmune disorders, in particular systemic lupus erythematosus (EP 0,217,206).

U.S. Pat. No. 4,061,767 describes the use of 2-hydroxyethylidene-cyanoacetanilide derivatives for the preparation of a pharmaceutical having anti-inflammatory and analgesic action.

Psoriasis is a special form of skin disorder characterized by the development of reddish plaques, which tend to be dry and scaly. Psoriasis occurs most frequently in adults. Manifestations of psoriasis range from a few lesions to widespread disease. Psoriatic lesions are caused by abnormally increased epidermal cell proliferation, e.g., proliferation of keratinocytes is enhanced. The disease causes exfoliation which, although unsightly and emotionally stressful, rarely compromises general health. In the U.S. in 1992 it is estimated that between 4 and 8 million people are affected with psoriasis. About 200,000 new cases of the disease are diagnosed annually. Psoriasis is a global problem; it has been reported that in Europe 1 to 2% of the population have this disease. The etiology of psoriasis remains elusive, although it appears to have an inherited component. Common types of psoriasis are:

- Vulgaris (Plaque) Chronic plaque psoriasis is usually treatable at home with emollients, tar, dithranol and topical corticosteroids. The mechanism of action appears most likely to be direct regulation of keratinocyte proliferation and differentiation. Skin irritation is frequently noticed by patients, but rarely requires discontinuation of treatment.
- Eruptive/Guttate Eruptive psoriasis in children and young adults is characterized by the acute development of multiple drop-like lesions following upper respiratory tract infection by beta-hemolytic streptococci.
- Erythrodermia Psoriasis may generalize to a severe, chronic condition, including erythema (flushing) and scaling of the entire skin, possibly caused by a Koebner phenomenon.
- Pustular Pustular psoriasis, which affects mostly adults, may be localized and chronic or, in more severe cases, generalized. Precipitating factors influencing both local and generalized forms include various drugs (e.g., lithium, hydrochloroquine), irritative topical therapy (e.g., coal tar), dental and upper respiratory infections, pregnancy and solar irradiation. Elimination of provoking factors is the first line of management.

The treatment of psoriasis is not entirely satisfactory. A large number of ointments and salves have been used, but the reaction to these is unpredictable. Frequently exposure to the sun or ultraviolet light will cause the condition to improve, often psoriasis fails to improve despite any form of therapy.

A promising therapeutic approach for the treatment of psoriasis is the use of immunosuppressive agents. Human studies using oral cyclosporine A to treat psoriasis have been in progress for nearly 9 years. Thousands of patients with severe psoriasis have been treated worldwide, with a high success rate. Like most potent drugs, cyclosporine A has a number of side effects, most of which are transient and not serious. The most limiting side effect, however, remains kidney dysfunction (Mason J, Pharmacol rev, 41: 423, 1989; Borel and Kis, Transplantation Proc., 23: 1867–1874, 1991).

Therapy with immunosuppressive agents is often associated with serious side effects such as toxicities, including neurotoxicity, hypertension, hypomagnesemia, anemia, leucopenia, thrombocytopenia, tendency to acquire infections, renal function impairment and teratogenicity.

In an attempt to develop better agents for the treatment of psoriasis is has been found that a compound of the formula I or II shows an effective inhibition of keratinocytes proliferation. The compounds of the formula I or II are well tolerated by human beings. During therapy of human beings no decreased resistance to infections, no kidney dysfunction, no relevant changes of laboratory values such as liver enzymes, blood count or body weight have been observed. The compounds of the formula I or II show a better risk benefit ration compared with other immunosuppressive agents, have a long lasting effect after withdrawal and offer the possibility of a short term therapy and longer remission intervals.

Therefore the invention relates to a method of preventing or treating a skin disorder in a patient in need thereof by administering an effective amount of a compound of the formula I or II

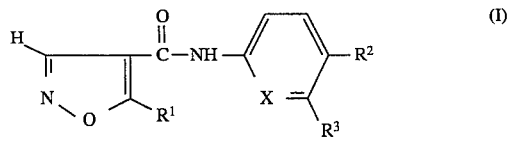

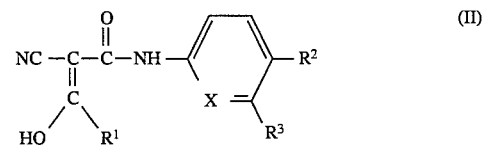

wherein $R^1$ denotes
   a) methyl,
   b) $(C_3-C_6)$-cycloalkyl,
   c) $(C_2-C_6)$-alkyl, having at least 1 double or triple bond between the carbon atoms,
$R^2$ denotes
   a) —$CF_3$ or
   b) —CN,
$R^3$ denotes
   a) $(C_1-C_4)$-alkyl or
   b) hydrogen atom,
X denotes
   a) —CH— group or
   b) nitrogen atom,
where the compound of the formula II is present as such or in the form of a physiologically tolerable salt.

Preferred are compounds of the formula I or II wherein $R^1$ denotes
   a) methyl,
   b) cyclopropyl or
   c) —$CH_2$—$CH_2$—C≡CH,
$R^2$ denotes —$CF_3$,
$R^3$ denotes methyl or hydrogen atom and
X denotes —CH— group.

Especially preferred is a compound of the formula I, wherein $R^1$ denotes methyl, $R^2$ denotes —$CF_3$, $R^3$ denotes hydrogen atom and X denotes carbon atom (N-(4 -trifluoromethylphenyl)-5-methylisoxazole-4-carboxamide), or a compound of the formula II, wherein $R^1$ denotes methyl, $R^2$ denotes —$CF_3$, $R^3$ denotes hydrogen atom and X denotes —CH— group (N-(4-trifluoromethylphenyl)-2-cyano-3-hydroxycrotonamide).

Suitable physiologically tolerable salts of the compound of the formula II are, for example, alkali metal, alkaline earth metal or ammonium salts, including those of physiologically tolerable organic ammonium bases.

The compounds of the formula I or II can be prepared by the following process:

A compound of the formula III

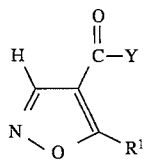
(III)

in which Y represents a halogen atom, preferably chlorine or bromine, is reacted with the amine of the formula (IV)

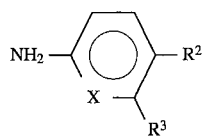
(IV)

to give the compound of the formula I, and this can then be reacted in the presence of a basic agefit to give the compound of the formula II.

The above-mentioned reactions are carried out under standard conditions in a known manner (EP 13,376; EP 484,223; EP 538,783; U.S. Pat. No. 4,061,767).

The starting substances for the reactions are known or can be easily prepared by methods known from the literature.

The invention also related to a successful medical treatment of eczema, dermatitis, dermatitis medicamentosa, dermatitis allergica, dermatitis toxica, dermatitis photoallergica and dermatitis atopica (atopically dermatitis).

The invention further relates to a method of inhibiting the proliferation of keratinocytes comprising administering an effective amount of a compound of the formula I or II or a physiologically tolerable salt of a compound of the formula II.

The invention also relates to a pharmaceutical which contains an effective amount of a compound of the formula I and/or a compound of the formula II, where the compound of the formula II is present as such or in the form of a physiologically tolerable salt, in addition to pharmaceutically suitable and physiologically tolerable excipients, diluents and/or other active substances and auxiliaries.

The invention also relates to a process for the preparation of a pharmaceutical for the treatment of psoriasis, which comprises bringing a compound of the formula I or II and/or a physiologically tolerable salt of compound of the formula II into a suitable administration form using a pharmaceutically suitable and physiologically acceptable excipient and, if appropriate, other suitable active substances, additives or auxiliaries.

The pharmaceutical according to the invention can be administered orally, topically, rectally or parenterally.

Suitable solid or liquid pharmaceutical administration forms are, for example, granules, powders, coated tablets, tablets, (micro)capsules, suppositories, syrups, juices, suspensions, emulsions, drops or injectable solutions and preparations having a protracted release of active substance, in whose preparation customary auxiliaries, such as excipients, desintegrants, binders, coating agents, swelling agents, lubricants, flavorings, sweeteners or solubilizers are used. Commonly used auxiliaries which may be mentioned are, for example, magnesium carbonate, titanium dioxide, lactose, mannitol and other sugars, talc, milk protein, gelatin, starch, cellulose and its derivatives, animal and vegetable oils, polyethylene glycols and solvents, such as, for example, sterile water and mono- or polyhydric alcohols, for example glycerol.

Preferably, the pharmaceutical preparations are prepared and administered in dosage units, each unit containing as the active constituent a certain dose of a compound of the formula I and/or II, where compound of the formula II is present as such or in the form of a physiologically tolerable salt. In the case of solid dosage units, such as tablets, capsules or suppositories, this dose can be up to about 500 mg, preferably 5 to 400 mg, 5 to 200 mg, 10 to 100 mg 10 to 25 mg.

For the treatment of a patient (70 kg) suffering from psoriasis in the early phases a loading dose of at most 600 mg per day, preferably 300 mg a day and in the later rehabilitation phases an oral administration of 3-times 200 mg per day, preferably 1-time 20 mg per day of N-(4-trifluoromethylphenyl)-5 -methylisoxazole-4-carboxamide and/or N-(4-trifluoromethylphenyl)-2-cyano-3 -hydroxycrotonamide are indicated.

Under certain circumstances, however, higher or lower doses may also be appropriate. The administration of the dose can be carried out both by singly administration in the form of an individual dosage unit or else several smaller dosage units and by multiple administration of subdivided doses at specific intervals.

Preventing includes the prophylactic prevention of psoriasis in a susceptible mammal and treating includes arresting the development, and retarding the progression of psoriasis in a susceptible mammal.

A compound of the formula I or II and/or its corresponding salts can also be combined during the preparation of the above-mentioned pharmaceutical administration forms together with other suitable active substances, for example antiuricopathics, thrombocyte aggregation inhibitors, analgesics and steroidal or non-steroidal antiinflammatories.

EXAMPLE 1

Preparation of N-(4-trifluoromethylphenyl)-5-methylisoxazole-4-carboxamide

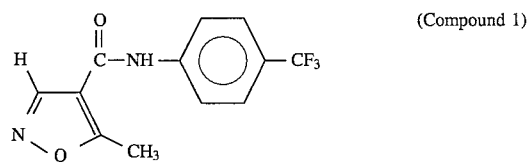
(Compound 1)

A solution of 0.05 mol of 5-methylisoxazole-4-carbonyl chloride (7.3 g) in 20 ml of acetonitrile is added dropwise at room temperature to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile each time, and the combined filtrates are concentrated under reduced pressure. 12.8 g of white, crystalline N-(4-trifluoromethylphenyl)-5-methylisoxazole-4-carboxamide (compound 1) are thus obtained.

EXAMPLE 2

Preparation of N-(4-trifluoromethylphenyl)-2-cyano-3-hydroxycrotonamide

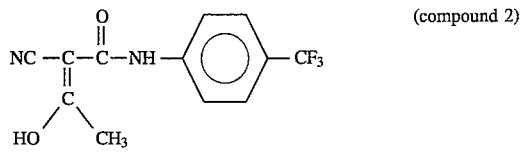
(compound 2)

0.1 mol of N-(4-trifluoromethylphenyl)-5-methylisoxazole-4-carboxamide is dissolved in 100 ml of methanol and treated at +10° C. with a solution of 0.11 mol (4.4 g) of sodium hydroxide in 100 ml of water. The mixture is stirred for 30 minutes and, after diluting with water, is acidified with concentrated hydrochloric acid. The precipitated crop of crystals is filtered off with suction, washed with water and dried in air. The yield is 24.4 g of N-(4-trifluoromethylphenyl)-2-cyano-3 -hydroxycrotonamide (compound 2). Melting point from methanol 205° to 206° C.

EXAMPLE 3

The following screen evaluates the ability of compounds to inhibit in vitro DNA synthesis by measuring the incorporation of the thymidine analog 5-bromo-2'-deoxy-uridine (BrdU)) into the DNA of replicating cells in culture.

Materials:
  Cells: Normal human epidermal keratinocytes (NHEK, Clonetics Corp., San Diego, Calif.).
  Labelling Reagent: Aqueous solution of 5-bromo-2'-deoxyuridine and 5-fluoro-2'-deoxyuridine (Amersham Corp., II).
  Anti-bromodeoxyuridine Antibody containing nuclease (Clone BU-1, Amersham Corp., II).
  Peroxidase-anti-mouse Immunoglobulin (Ig from pooled sheep antisera, Amersham Corp., II).
  Peroxidase substrate: ABTS [(2,2'-azino-di-(3-ethyl-benzthiazoline sulphonate)] Amersham Corp., II).
  Compounds: Compounds are dissolved in absolute ethanol (final concentration≦0.1%). Various drug concentrations are prepared in thymidine free keratinocyte growth medium (KGM without hydrocortisone, Clonetics Corp., Calif.) in the presence of BrdU.
  Dynatech MR 7000 microplate reader with 410 nm filter.
  Phosphate buffered saline (PBS) in 1 liter $H_2O$.
  11.5 g $Na_2HPO_4$
  2.96 g $NaH_2PO_4 \cdot 2H_2O$
  5.84 g NaCl
Tween-20 (Sigma)
Bovine Serum Albumin (BSA; Sigma)
Acetic Acid/ethanol fixative
  50 ml glacial acetic acid
  900 ml ethanol
  50 ml water
Stopping Agent (100 ml)
  0.01 g sodium azide
  2.10 g citric acid monohydrate
Method:
  Keratinocytes are seeded into 96-well flat bottom (6.4 mm diameter) culture dishes at 5,000 cells/well. The cells are allowed to grow (2–3days) and then dosed with various concentrations of compounds prepared in KGM without thymidine, without hydrocortisone in the presence of BrdU (1:200). After 18–24 hours at 37° C., 5% $CO_2$, the cells are washed with warm PBS and fixed with acetic acid/ethanol for 30 minutes at room temperature. After washing the wells with PBS/0.1% Tween-20, the remaining electrostatic sites on the polystyrene plates are blocked by 3% BSA in PBS/0.1% Tween-20. Anti-bromodeoxyuridine antibody solution with nuclease for denaturing DNA is added to each well and allowed to incubate for 2 hours at 37° C., 5% $CO_2$. The plates were again washed with PBS/0.1% Tween-20 and then incubated at room temperature with peroxidase lined anti-mouse immunoglobulin (1:600). After washing off the second antibody, 1 mM ABTS substrate solution is added to all wells until the desired color intensity (green) is achieved. The color development is stopped by the addition of a Stopping Agent. The absorbance is then measured at 410 nm with a microplate reader using cells in wells not exposed to BrdU as blanks.

Results:
  The intensity of the color reaction is proportional to the BrdU incorporated by proliferating cells. The amount of BrdU incorporated in treated cells in wells is compared to those of untreated controls as follows:

$$\frac{\% \text{ change}}{\text{from Control}} = \frac{X \text{ Absorbance 410 nm treated cells}}{X \text{ Absorbance 410 nm Control}} \times 100 \, (-100)$$

TABLE 1

| | inhibition of nhek proliferation (BRDU) | | | |
|---|---|---|---|---|
| Compound | Dose (M) | % Inhibition | Significance | $IC_{50}$ (μM) |
| 1 | $10^{-4}$ | 87 | p < 0.01 | |
|   | $10^{-5}$ | 22 | NS | |
|   | $10^{-6}$ | 12 | NS | 18.0 |
| 2 | $10^{-4}$ | 84 | p < 0.01 | |
|   | $10^{-5}$ | 49 | p < 0.05 | 15.5 |

$IC_{50}$ is inhibition concentration; NS is not significant.

EXAMPLE 4

Acute toxicity after intraperitoneal administration

The acute toxicity after intraperitoneal administration of the test substances was determined with NMRI mice (20 to 25 g) and SD rats (120 to 195 g). The test substance was suspended in a 1% strength sodium carboxymethylcellulose solution. The different dosages of the test substance were administered to the mice in a volume of 10 ml/kg of body weight and to the rats in a volume of 5 ml/kg of body weight. Per dosage, 10 animals were used. After 3 weeks, the acute toxicity was determined by the method of Litchfield and Wilcox. The results are summarized in the table 2.

TABLE 2

| | Compound 1 acute toxicity intraperitoneal $LD_{50}$ (mg/kg) | Compound 2 acute toxicity intraperitoneal $LD_{50}$ (mg/kg) |
|---|---|---|
| NMRI mouse | 185 (163–210) | 150 (100–200) |
| SD rat | 170 (153–189) | |

EXAMPLE 5

Double blind study with human beings

In a randomized double blind study with 400 human beings the patients received a 5, 10 and 25 mg of compound 1 daily maintenance therapy for 6 months preceded by a single initial dose of 50, 100 and 100 mg respectively. During this study urine analysis of the human beings showed no kidney dysfunction (no nephrotoxicity).

We claim:

1. A method of treating a skin disorder selected from the group consisting of psoriasis, dermatitis, and eczema which comprises administering to a recipient an effective amount of a pharmaceutical composition containing as an active ingredient a compound of the formula I or II

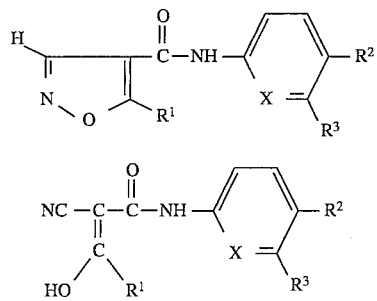

wherein $R^1$ denotes
  a) methyl,
  b) $(C_3-C_6)$-cycloalkyl, or
  c) $(C_2-C_6)$-alkyl, having at least 1 double or triple bond between the carbon atoms,
$R^2$ denotes
  a) —$CF_3$ or
  b) —CN,
$R^3$ denotes
  a) $(C_1-C_4)$-alkyl or
  b) hydrogen atom, and
X denotes
  a) —CH— group or
  b) nitrogen atom
where the compound of the formula II may optionally be present in the form of a physiologically tolerable salt.

2. The method of claim 1, wherein the compound of the formula I or II is selected from the group consisting of $R^1$ denotes
  a) methyl,
  b) cyclopropyl or
  c) —$CH_2$—$CH_2$—C≡CH,
$R^2$ denotes —$CF_3$,
$R^3$ denotes methyl or hydrogen atom and
X denotes —CH— group.

3. The method of claim 1, wherein a compound is selected from the group consisting of N-(4-trifluoromethylphenyl)-2-cyano-3-hydroxycrotonamide and N-(4-trifluoromethylphenyl)-5-methylisoxazole-4-carboxamide.

4. The method of claim 1, wherein said skin disorder is psoriasis selected from the group consisting of psoriasis vulgaris, psoriasis eruptive, psoriasis erythrodermic, and psoriasis pustular.

5. The method of claim 1, wherein said skin disorder is psoriasis.

6. The method of claim 1, wherein said composition is administered intravenously, orally, topically, or parenterally.

7. The method of claim 1, wherein said composition is administered in a solid dosage unit of up to about 500 mg.

8. A method of treating skin disorders resulting from the proliferation of keratinocytes which comprises inhibiting said proliferation by administering to a patient in need of such treatment an effective amount of a pharmaceutical composition containing as an active ingredient a compound of the formula I or II as defined in claim 1, wherein said skin disorders are selected from the group consisting of psoriasis, dermatitis, and eczema.

9. The method of claim 8, wherein said skin disorder is psoriasis selected from the group consisting of psoriasis vulgaris, psoriasis eruptive, psoriasis erythrodermic, and psoriasis pustular.

10. The method of claim 8, wherein said composition is administered intravenously, orally, topically, or parenterally.

11. The method of claim 8, wherein said skin disorder is psoriasis.

12. The method of claim 11, wherein said psoriasis is selected from the group consisting of psoriasis vulgaris, psoriasis eruptive, psoriasis erythrodermic, and psoriasis pustular.

13. The method of claim 8, wherein said skin disorder is dermatitis.

14. The method of claim 13, wherein said dermatitis is selected from the group consisting of dermatitis atopica, dermatitis allergica, dermatitis photoallergica, and dermatitis medicamentosa.

15. The method of claim 1, wherein said skin disorder is dermatitis.

16. The method of claim 15, wherein said dermatitis is selected from the group consisting of dermatitis atopica, dermatitis allergica, dermatitis photoallergica, and dermatitis medicamentosa.

* * * * *